United States Patent [19]

Hee

[11] Patent Number: 4,878,148
[45] Date of Patent: Oct. 31, 1989

[54] CROCHETED FABRIC ELASTIC WRIST BRACELET BEARING AN INTERIOR CONDUCTIVE YARN

[75] Inventor: Roland Hee, Manilla, Philippines
[73] Assignee: JES, LP, Newport Beach, Calif.
[21] Appl. No.: 76,306
[22] Filed: Jul. 22, 1987
[51] Int. Cl.[4] ............................................... H05F 3/02
[52] U.S. Cl. .................................... 361/220; 57/901; 439/37; 66/193
[58] Field of Search .................. 361/212, 220; 439/37; 57/901; 66/193

[56] References Cited

U.S. PATENT DOCUMENTS

| | | | |
|---|---|---|---|
| 3,377,509 | 7/1967 | Legge | 361/220 X |
| 3,422,460 | 10/1966 | Burke et al. | 57/901 X |
| 3,424,698 | 1/1969 | Lupinski et al. | 252/500 |
| 3,459,997 | 8/1967 | Legge | 361/223 |
| 3,541,389 | 12/1968 | Van Name | 361/224 |
| 3,582,488 | 6/1971 | Okuhashi et al. | 57/901 X |
| 3,596,134 | 7/1971 | Burke | 361/220 |
| 3,699,590 | 10/1972 | Webber et al. | 361/220 X |
| 3,812,861 | 5/1974 | Peters | 361/220 X |
| 3,832,841 | 9/1974 | Cole | 57/207 |
| 3,851,456 | 12/1974 | Hamada et al. | 57/901 X |
| 3,857,397 | 12/1974 | Brosseau | 361/220 |
| 3,904,929 | 9/1975 | Kanaya et al. | 361/220 |
| 3,986,530 | 10/1976 | Maekawa | 57/901 X |
| 3,987,613 | 10/1976 | Woods et al. | 57/901 X |
| 4,267,233 | 5/1981 | Tanaka et al. | 57/901 X |
| 4,321,789 | 3/1982 | Dammann et al. | 51/224 X |
| 4,373,175 | 2/1983 | Mykkanen | 361/220 |
| 4,398,277 | 8/1983 | Christiansen et al. | 361/220 |
| 4,402,560 | 9/1983 | Swainbank | 439/37 |
| 4,420,529 | 12/1983 | Westhead | 57/901 X |
| 4,422,483 | 12/1983 | Zins | 57/901 X |
| 4,475,141 | 10/1984 | Antonevich | 361/220 |
| 4,577,256 | 3/1986 | Breidegam | 361/220 |
| 4,639,825 | 1/1987 | Breidegam | 361/212 |
| 4,654,748 | 3/1987 | Rees | 361/220 |

FOREIGN PATENT DOCUMENTS 2547390 10/1975 Fed. Rep. of Germany .

Primary Examiner—L. T. Hix
Assistant Examiner—Brian W. Brown
Attorney, Agent, or Firm—Stetina and Brunda

[57] ABSTRACT

A crocheted fabric is formed of electrically insulating elastic yarn interlocked to a wefting yarn by a warping yarn. The crocheted fabric bears on its one surface which is disposed toward the skin plural strands of conductive yarn. This conductive yarn is interlocked to the crocheted fabric by the warping yarn. It proceeds in a serpentine path along the long axis of the grounding strap. The interior surface of the wrist bracelet bearing this prominent, and visually inspectable, conductive yarn provides reliable electrical contact to the skin. Meanwhile, the outer surface of the grounding strap reliably maintains electrically insulating qualities.

13 Claims, 2 Drawing Sheets

CROCHETED FABRIC ELASTIC WRIST BRACELET BEARING AN INTERIOR CONDUCTIVE YARN

BACKGROUND OF THE INVENTION

1. Field of the Invention

The present invention generally pertains to electrically conductive bracelets worn on the ankle or wrist to drain or wick static electrical charge from the wearer. The present invention specifically concerns stretchable elastic fabric bracelets with an insulating surface upon the external circumference of the bracelet.

2. Description of the Relevant Art

As reported in U.S. Pat. No. 4,577,256, static electricity causes problems in the electronics and other industries, particularly with the advent of integrated circuits and other microelectronic components. Components such as integrated circuits, for instance, may be disabled or destroyed by over-voltage or power density resulting from static electricity. Certain junctions in such circuits can be destroyed by as little as a 50-volt potential, which radically changes the doping structure in their lattices. Power densities resulting from excessive potential and imperfections in a silicon circuit layout or structure can vaporize or radically alter the silicon substrate and thus impair or destroy a circuit's performance. Yet a person walking on a carpet on a dry day can accumulate as much as 30,000 volts of potential, and he can triboelectrically generate thousands of volts by simply changing his position in his chair or handling a styrofoam cup.

Such a person can inadvertently discharge static electric potential into a circuit or component by touching it and causing overvoltage or excessive power density. Additionally, the potential in such a person's body can induce a charge in a circuit that can later cause overvoltage or excessive power density when the circuit is subsequently grounded. More and more frequently, therefore, personnel in industries in which integrated circuits and other microelectronic components are handled or assembled are taking measures to limit the failure rate of those circuits and components by attempting to keep both themselves and their environment at a zero electrical potential. Such measures include providing workers and work stations with antistatic carpet; conductive or dissipative grounded desk top work surfaces; hot air ion generators which emit ions to neutralize static charges; and grounding straps worn by workers to keep workers at zero potential. The term "conductive" herein, and according to its customary usage in the art, means an electrical resistance of between zero and $10^5$ ohms. Similarly, "dissipative" means a resistance of between $10^5$ and $10^9$ ohms, "anti-static" means a resistance of between $10^9$ and $10^{14}$ ohms, and "insulative" means a resistance of more than $10^{14}$ ohms.

With specific relation to grounding strap measures grounding strap must have several features in order to perform its grounding function effectively. First, it must ensure that the wearer's skin is electrically connected to ground. This connection is typically accomplished by a conductive surface on the inside of a strap contacting the skin. The conductive surface is electrically connected to a grounding cord which leads from the strap to a grounded electrical connection. If the electrical contacting means on the inside of the strap becomes dirty or fouled by oil, perspiration or hair, then the strap may lose its effectiveness. It is therefore important to use a conductive material on the inner surface of the strap that does not easily become dirty or fouled.

Secondly, user comfort is a premier consideration because if the strap is uncomfortable, then the wearer will be tempted to remove it and can thereby cause damage to electrical components on which he is working. A strap that is easily stretchable, that is attractive and that poses minimum inconvenience to the wearer is therefore highly desired.

The situations in which grounding wrist straps are used heightens the importance of their being comfortable so that they are continuously worn and maintain continuous electrical contact with the skin. A person working on microelectronic components or integrated circuits may be completely unaware that he has accumulated minor static electrical discharges, and may therefore unknowingly be in a position to disable circuits on which he is working or which he is handling. If his strap is loose or he has removed it, he may be unaware that electrical discharges transmitted from his fingers are disabling these circuits. (A typical person cannot sense a static electrical discharge of less than approximately 3,500 volts.) No one may discover that the circuits have been disabled or damaged until hours, days or weeks later, when the circuits have been placed in components or devices which fail in the field. Removal and repair or replacement of these circuits once in the field is far costlier than avoiding potential failure while the wearer is handling the circuits. Thus, a manufacturer typically must depend upon the effectiveness of the wrist strap to maintain a lower failure rate of such electronic circuits and components, by maintaining continuous electrical contact with the wearer's wrist and by providing minimum temptation to remove the strap from his wrist.

Finally, grounding wrist straps should be electrically insulating on their exterior surfaces (at least in all areas wherein electrical connection is not intentionally made for the wicking of electrical charge to ground) in order that the hazard to the wearer from inadvertant contact of the bracelets surface with a source of electrical potential should be reduced. The interior circumferential surface of a grounding strap is intentionally made to be an excellent electrical conductor and be incontact with the user. If the bracelet's outer surface were to be conductive, and were in electrical contact with the inner circumferential surface, then an efficacious, and hazardous, path of electrical current conduction to the body might be presented. This path would generally be of lower resistance that that presented by the naked skin. Furthermore, if the bracelet's outer surface were to catch or snag on a source of electrical energy then a wearer might be detrimentally placed in contact with this source for a longer period of time than would otherwise be the case.

These considerations of selective conductivity and of comfort have been recognized, and have been addressed, by several types of grounding straps. A first type of grounding straps are made of metal. U.S. Pat. No. 4,373,175 issued Feb. 8, 1983 to Mykkanen, for instance, discloses an extensible metal band similar to an expansion watchband on which a snap fastener for a grounding cord is attached. Such a strap can be reasonably comfortable. However, its conductive metal outer surface can prove dangerous to the wearer if it contacts an electrical potential sufficient to electrocute the wearer.

U.S. Pat. No. 4,402,560 issued Sept. 6, 1983 to Swainbank discloses an expansive metal conductive wrist strap improved for having a resistor, enclosed within a housing, in the ground lead at a point proximate the point of plugged electrical connection to the wrist strap. The housing is adapted to be grasped by the fingers for plugging and unplugging the ground lead from the wrist strap.

Another, second, type of prior art grounding straps is made of textile material In one such all-textile strap the textile is impregnated with a thermosetting conductive coating and fastened about the wrist of an operator. The fabric grounding strap is connected by way of a swivel type snap connector and insulated conductor to a suitable device for making a connection to ground at the work station.

One fabric grounding strap reportedly improved for comfort is disclosed in U.S. Pat. No. 3,857,397 to Brosseau. Outer and inner conductive polyolefin layers sandwich an intermediate nylon scrim layer to form the band. Hook and loop (Velcro ®) fastening materials can accumulate on such surfaces and interfere with electrical contact between the band and the skin. Further, carbon particles tend to wear off onto the wrist, causing black stripes on the wrist. The nonstretchable nature of such bands means that the wearer must adjust then to be tight enough to cause sufficient elecrical contact, but loose enough to be comfortable, and skin contact can be lost or intermittent.

Another approach is disclosed in U.S. Pat. No. 4,398,277 to Christiansen and Westberg ("Christiansen"). This strap is made of knitted stretchable fabric containing stainless steel fibers. A plastic and metal fitting permanently closes the strap into a loop of predetermined size and also has a connection for a grounding cord. This strap can prove uncomfortable to the wearer, however, unless his wrist comports with the predetermined strap size offered by the manufacturer. Further, the knitted fabric permits the strap to roll over on itself as it is being pulled over the hand and causes the strap to become thinner as it is stretched. Because the fabric is knitted, it can also "pull" and "run" when snagged. Perhaps more important it has been discovered that the electrical conductivity of the Christiansen strap decreases as the strap is relaxed, and thus varies from one stretched state to another. This phenomenon probably occurs because the metallic strands in the conductive yarns are pulled more tightly together in the knitted material as it is stretched, and are separated from one another to a certain extent in the knitted conductive yarns as the strap is relaxed.

A reported solution to some of these problems with grounding wristbands made of fabric is discussed in U.S. Pat. No 4,577,256 to Breidegam. A woven stretchable grounding strap is shown which uses conductive fibers on the inside surface of the strap to contact the skin and to conduct electrical charges to a grounding cord attached to the strap. Face yarns exposed on the outer surface are woven to form designs. The woven fabric material of the strap is attached to a clasp allowing the strap to be adjustable in size. Because of the woven nature of the fabric material and the adjustable clasp, the strap is reported to be more comfortable than other conductive elastic wrist straps. The woven fabric material is also reported to be advantageous because it stretches easily, it is relatively inexpensive, and it does not roll over onto itself as it is being drawn over the hand. This woven stretchable grounding strap is in actual industrial usage circa 1987.

This prior art fabric wristband described in the Breidegam patent—which is visually similar to the fabric elastic wrist bracelet in accordance with the present invention—has been found, however, to be subject to latent defects, causing failure of function, during manufacture and use. Specifically, the construction of the Breidegam prior art wristband by the process of weaving innately requires that the conductive thread, or yarn, which is necessary for the wristband's conductive function should be interlaced to and extend through, the inner and the outer, sides of a fabric body, or garter. Because electrical conductivity is desired upon only one side (the inner side) of the wristband, additional face yarn is applied over the outer side in order to prevent the conductive yarn from emerging. The effectiveness of insulating one layer of electrically conductive yarn by an overlying layer of another, electrically insulating yarn, during manufacture has proven to be poor and unreliable. Worse, since the wristband is necessarily stretched and contracted during fitting and use, the face yarn loosens and shifts thereby allowing the conductive yarn to progressively intermittently emerge in sporadic areas. Because this emergence which produces increased conductivity at the outer surface of the wristband has no detrimental effect on the wristband's primary conductive function to wick electrical charge, it may go unnoticed and/or ignored by the wristband user. However this latent increase in conductivity of the wristband's outer surface can have severe safety consequences if, and when, the supposed insulating qualities of the outer surface are ever called upon to protect the user from electrical shock. Since periodic electrical testing of fabric grounding straps for their insulative, as opposed to their conductive, properties seems to be cumbersome, of uncertain efficacy, and incompatible with the in-line use and use environment of the straps, it is highly desirable that the problem of latent outer surface conductivity should be definitively solved, and not merely recognized in order that it might be abated.

SUMMARY OF THE INVENTION

The present invention is embodied in a crocheted fabric elastic wrist bracelet, or wristband, which connects via a pluggable grounding cord to an electrical ground for draining static electrical charge from the wearer of such wrist bracelet. In accordance with the present invention, the fabric of the wristband is crocheted and includes both warp and weft yarn interlocked to an elastic garter. The garter and the yarns are electrically insulating. Entirely upon a one side of the crocheted fabric, and adhered thereto by "hooks", or loops, formed by the warping yarn are a plurality of serpentine strands of conductive yarn. This conductive yarn, borne upon and interlocked to the matrix of the crocheted fabric, provides an electrically conductive path exclusively on the interior of the wrist bracelet. The serpentine electrically conductive yarn is not subject to being exposed to the exterior of the wrist bracelet, which remains electrically insulating under all normal conditions of use and wear. The serpentine electrically conductive yarn protrudes above the matrix of the crocheted fabric and makes excellent electrical contact with the skin. The serpentine electrically conductive yarn is visually pronounced, and may be visually inspected for continuity which indicates the operativeness of its electrically conductive function.

It is therefore an object of the present invention to provide an inexpensive crocheted fabric wrist bracelet for service as a grounding strap. This crocheted fabric bracelet is more effective in preserving an electrically conductive path on the interior of such bracelet, while simultaneously insuring an electrically insulating condition to the exterior of such bracelet, then are other prior art knitted or woven fabric bracelets. Further objects of the present invention include that the crocheted fabric elastic bracelet should be comfortable and adjustable in size, durable during use, attractive, not subject to distortion or roll over or permanent stretching during donning or use, and susceptable of being laundered.

BRIEF DESCRIPTION OF THE DRAWINGS

These and other objects, features, and advantages of the preset invention will become more apparent upon reference to the following drawings and accompanying specification wherein.

DESCRIPTION OF THE PREFERRED EMBODIMENT

Figure 1:
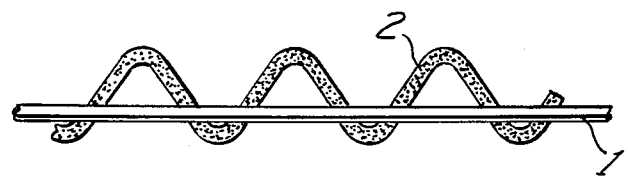
FIG. 1 is a side view of a prior art woven fabric for stretchable grounding straps.
Figure 2:
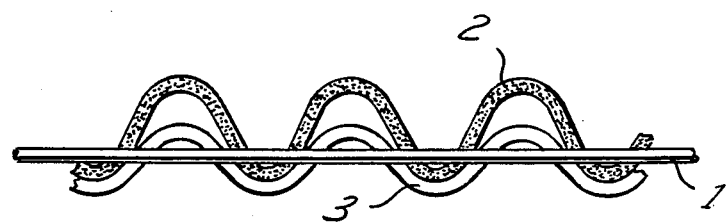
FIG. 2 is a side view of a prior art woven fabric for stretchable grounding straps, particularly showing the inclusion of conductive yarn within such woven fabric.

The present invention is an improvement upon prior art electrically conductive wrist bracelets which are made of woven fabric material The woven fabric wrist bracelets are themselves an improvement upon prior art wrist bracelets made of knitted fabric material. A prior art woven fabric used in a wrist bracelet is illustrated in side view in FIGS. 1 and 2. By definition, a woven cloth is made by interlacing a series of warp and filling threads, or yarns, at right angles. In producing woven fabric for stretchable conductive wrist bracelets, or grounding straps, a rubber thread, or yarn, 1 forms a garter portion of the woven cloth. A conductive yarn 2 is made to interlace with this body so as to form loops on both sides of the body. Within FIGS. 1 and 2, the larger loops of conductive yarn 2 on the upper side of the garter made from rubber thread 1 are intended to be disposed toward the interior of the grounding strap, and in electrical contact with the wrist. Since the conductive yarn 2 also, undesirably, appears upon the opposite, exterior, side of the grounding strap then it must be prevented from emerging at the surface of this exterior side if this side is to be made electrically insulating. The manner by which this is accomplished is disclosed in U.S. Pat. No. 4,577,256 to Breidegam and the disclosure of which is expressly incorporated herein by reference is illustrated in FIG. 2. A face yarn 3 is woven on top of the conductive yarn 2 at a one side of the fabric in order to shield such conductive yarn 2, and in order to prevent it from emerging at that side of the fabric. It is this face yarn which is often made to form a graphic, or pictorial, design on the exterior of the stretchable grounding strap made from woven fabric.

The prior art woven cloth particularly for use in stretchable electrically conductive grounding straps, which cloth was shown in FIG. 2, possesses potential problems in establishing, and in maintaining, electrically insulating properties at its exterior side. If the face yarn 3 is not properly applied in total and complete coverage of the conductive yarn 2 then there may be small areas, or threadlets, of the conductive yarn 2 which emerge, or which are contactable, through the face yarn 3. Furthermore, after the band is stretched several times along the longitudinal axis of rubber garter thread 1, then the tension of both the conductive yarn 2 and the face yarn 3 is equalized, or "loosened up", and the conductive yarn 2 will tend to assume the same loop size as the face yarn 3, and emerge therefrom. At this point, the woven fabric is essentially electrically conducting on both sides, although, due to relative placements of the face yarn 3 and conductive yarn 2, it may be some what better conducting, as is desired, on its interior surface (towards the top in FIGS. 1, 2). Furthermore, if the conductive yarn 2 breaks, especially in a location where at it is shielded by face yarn 3, then this break, and commensurate deterioration of the electrically conductive properties of the bracelet, may not be immediately visible. In summary, the woven stretchable fabric for use in electrically conductive ground straps suffers from a change in the electrical properties of its two sides over time and use, and may come to exhibit latent defects in both its insulating and conductive properties which defects are not immediately apparent to the wearer-user of the grounding strap.

The preferred embodiment of a crocheted fabric elastic wrist bracelet bearing conductive yarn upon its interior in accordance with the present invention is generally shown in FIGS. 3-6. As is most particularly illustrated in FIGS. 4-6, the yarns which form a crocheted fabric are by definition, not interlaced with each other. This means that the conductive yarn need not go in and out of the body of the band as is the case with conductive yarn 2 in the prior art woven cloth shown in FIGS. 1 and 2 The conductive yarn in the crocheted fabric of the present invention is rather borne upon, or "floating" upon, or attached to only one side of the crocheted fabric body. The attachment is via "hooks" formed by the crocheting process, or by the series of interlocking chains formed by the crocheting process. By this manner of construction several advantages are realized.

Figure 6:
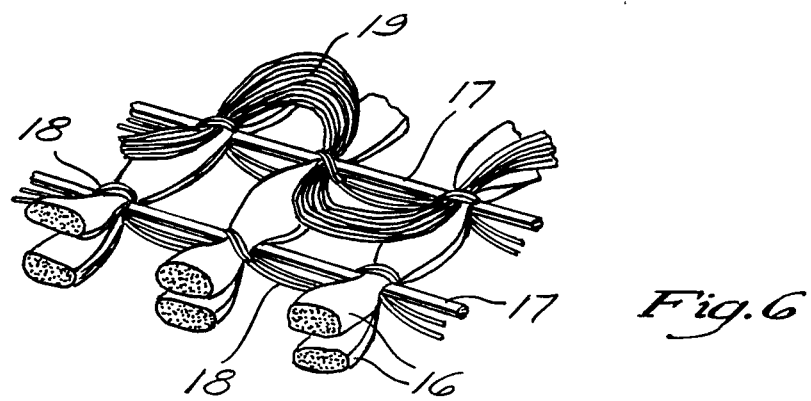
FIG. 6 is a detail perspective view particularly showing the manner by which conductive yarn is born upon the matrix of crocheted fabric within the preferred embodiment of the elastic wrist bracelet in accordance with the present invention.

As specifically shown in FIG. 6, upper and lower weft yarns 16 generally traverse between the opposing transverse edges of the wristband, thereby generally respectively forming upper and lower surfaces thereof. A plurality of elastic threads 17 extend longitudinally between the upper and lower weft yarns 16. A plurality of electrically conductive yarns 19 are connected to the wristband and are positioned beneath the lower weft yarns 16. Warp yarns 18 form an interlocking series of loop stitches which bind the upper and lower weft yarns 16 with the elastic threads therebetween and also serve to connect the electrically conductive yarns 19 to the underside of the wristband.

Figure 3:
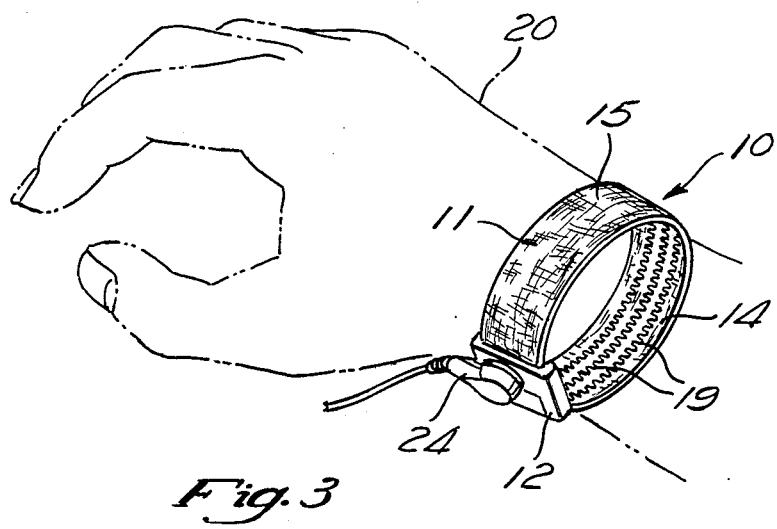
FIG. 3 is a perspective view of a preferred embodiment of the crocheted fabric elastic wrist bracelet in accordance with the present invention.

An overall perspective view of the preferred embodiment of a wrist bracelet 10 in accordance with the present invention is shown in FIG. 3. In its general appearance, the wrist bracelet 10 is visually similar to prior art woven grounding straps However, in accordance with the present invention, the fabric material 11 which is connected to a clasp 12 in order to form the wrist bracelet 10 is crocheted. An electrically conductive connector (not shown) is mounted centrally within the electrically insulating clasp 12, and connects the inner surface 14 of the wrist bracelet 10 to the grounding cord 24. The grounding cord 24 normally snaps to the electrical connector of wrist bracelet 10, contains a one megaohm resistor to prevent electric shock if it were to inadvertently contact a power source, is connected to an electrical ground or sink, and is the path by which electrostatic charges are wicked from the wrist of wearer 20 to ground.

Figure 4:
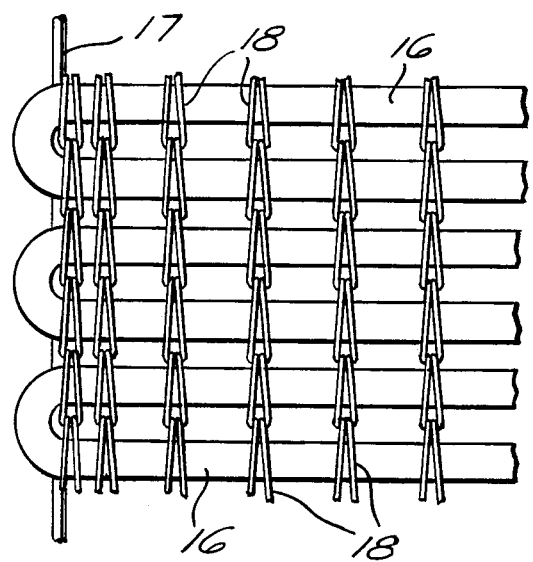
FIG. 4 is an enlarged plan view of the crocheted fabric used toward the exterior of the preferred embodiment of the elastic wrist bracelet in accordance with the present invention.
Figure 5:
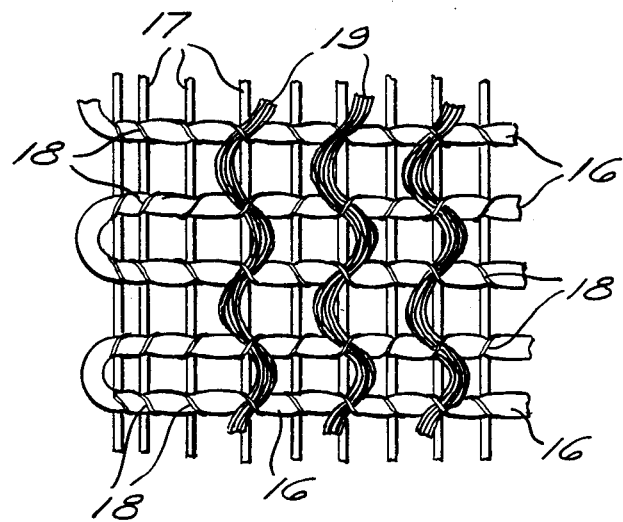
FIG. 5 is an enlarged plan view of the crocheted fabric used toward the interior of the preferred embodiment of the elastic wrist bracelet in accordance with the present invention.

The detailed structure of the crocheted fabric 11 of the preferred embodiment of the wrist bracelet 10 in accordance with the present invention is shown in FIGS. 4-6. A view of the external surface 15 to fabric 11 of wrist bracelet 10 is shown if FIG. 4. An elastic thread or yarn, 17 forming a garter is disposed along the long axis of the wrist bracelet 10. The elasticity of this thread 17 allows the wrist bracelet 10 to stretch. In accordance with the crocheting process, a wefting yarn 16 is affixed to the garter made from elastic yarn 17 by a warping yarn 18. In accordance with the definition of crochet needlework, the warping yarn 18 is formed into an interlocking series of loop stitches which are formed by an single thread and a hook needle. The crocheted fabric so formed upon an elastic garter is readily capable of stretching along the axis of the elastic threads 17 of the garter. The crocheted fabric also presents more open, or void, areas than does woven or knitted fabric. The void areas are useful for allowing the skin to breathe through a wrist bracelet formed of such fabric. The wefting yarn 16, elastic yarn 17, and warping yarn 18 are all electrically insulating.

An interior side 14 to the crocheted fabric 11 used in the wrist bracelet 10 is illustrated in enlarged plan view in FIG. 5, and in detailed perspective view in FIG. 6. In accordance with the present invention, the crocheted fabric formed from electrically insulating wefting yarn 16, elastic yarn 17, and warping yarn 18 bears upon its interior surface plural strands of conventional conductive yarn 19. These strands are in a serpentine configuration along the long axis of the wrist band 10 and are adhered thereto by being looped by the warping yarn 18. The conductive yarn 19 is entirely upon the surface of a one side of the matrix consisting of the crocheted cloth. In this exposed and protruding position it is held prominently and reliably in contact with the human skin for forming electrical contact thereto during use of wrist bracelet 10.

The conductive yarn 10 will not migrate through the crocheted fabric 11 during stretching and use of the wrist bracelet 10. Therefore the exterior surface 15 will remain insulating while the interior surface 14 remains electrically conductive. The serpentine path of the conductive yarn 19 allows it to readily expand and contract along the longitudinal axis of the wrist bracelet 10. The conductive yarn 19 is preferably made in a contrasting color to elastic yarn 17, warping yarn 18 and/or wefting yarn 16. In its postition borne and carried upon the crocheted fabric, it is then visually prominent. If one or more strands of the conductive yarn 19 come to be severed, breaking the electrical continuity thereof, then this severance will be immediately detectable by visual inspection of interior surface 14 to the wrist bracelet 10. Therefore the wrist bracelet 10 in accordance with the present invention is not prone to incur latent defects regarding the differing electrical conductivity of its two sides. However, should changes or deterioration in the selective electrical conducting and insulating functions occur, then these changes will be immediately visually detectable.

In accordance with the preceding discussion, certain variations in the crocheted fabric elastic wrist bracelet in accordance with the present invention will be perceived to be possible For example, the conductive yarn need not proceed in a serpentine path directly along the long axis of the wrist bracelet 10 and elastic yarn 17, but could proceed in a zig-zag course upon the interior surface 14 of the wrist bracelet 10. Various colors and finishes to the various threads can be employed. Therefore, in accordance with these and other possible variations, the present invention should be interpreted by the following claims, only, and not solely in accordance with that particular preferred embodiment within which it has been taught.

What is claimed is:

1. A strap for establishing electrical contact with a person's body, comprising:
   a length of crocheted material, extendable in its longitudinal direction circumferentially about a person's limb, said length of crocheted material comprising:
      a fabric body having an upper surface and a lower surface, said fabric body comprising at least one elastic yarn forming a garter oriented in the longitudinal direction to allow the material to stretch, at least two weft yarns, each running generally perpendicular to and disposed on opposite sides of said at least one elastic yarn so as to form the said upper and lower surfaces of said fabric body and at least one warp yarn affixing said weft yarns to said elastic yarn;
      an electrically conductive yarn hooked to said lower surface of the fabric body by the warp yarn; and
   an electrical connector making electrical connection to the conductive yarn;
   wherein the electrically conductive yarn is disposed toward the person's limb for making electrical contact therewith;
   wherein the electrically insulating yarns are disposed away from the person's limb for presenting an electrically insulating surface between the person's limb and the electrically conductive yarn.

2. The strap according to claim 1 wherein the electrically conductive yarn further comprises:
   a plurality of spaced parallel yarn lengths oriented substantially in the longitudinal direction.

3. The strap according to claim 2 wherein the plurality of spaced parallel yarn lengths proceed along their substantially longitudinal orientations in serpentine paths, which serpentine paths accord the yarn lengths the capability to extend and to contract in the longitudinal direction.

4. The strap according to claim 1 wherein the conductive yarn is adequately visible upon the one side of the fabric body to which it is hooked so as to allow visual determination of the physical and electrical continuity of the yarn.

5. The strap according to claim 4 wherein the conductive yarn is of a contrasting color to any of the elastic yarn and the wefting yarn and the warping yarn in order to facilitate the visual determination.

6. A method of making a fabric strap which is electrically insulating on its one side and which is electrically conductive on its other side, the method comprising:
   crocheting a fabric strap from an electrically insulating base yarn aligned in the long axis of the strap, from an electrically insulating wefting yarn substantially perpendicular to the base yarn, and from an electrically insulating warping yarn connecting the base yarn and the wefting yarn with interlocking looped stitches; and
   hooking an electrically conductive yarn to the surface of the fabric strap by the interlocking looped stitches of the warping yarn;
   wherein a one side of the fabric strap which does not hook the electrically conductive yarn is electrically insulating;
   wherein the other side of the fabric strap which does hook the electrically conductive yarn is electrically conductive.

7. The method according to claim 6 wherein the crocheting is of elastic base yarn and wherein the hooking is of conductive yarn in a serpentine path substantially along the axis of the strap, whereby the strap is elastically stretchable even though the wefting yarn, the warping yarn, and the conductive yarn need not be elastic.

8. An elastic fabric strap with an electrical connector affixed thereto for being elastically locatable about a person's appendage for making electrical contact via the connector to the body of the person CHARACTERIZED IN THAT:
   the elastic strap is crocheted of an electrically nonconductive garter and a wefting yarn and a warping yarn;
   the crocheted elastic fabric strap hooks upon a one side thereof by an interlocking chain of the warping yarn a substantially longitudinal electrically conductive yarn;
   the conductive yarn is disposed circumferentially toward a person's appendage upon an elastic embrace of the strap thereabout such appendage;
   the non-conductive crocheted strap is disposed circumferentially away from the person's appendage upon the elastic embrace of the strap thereabout such appendage; and
   electrical connection is made from the circumferentially interior conductive yarn to an electrical connector affixed circumferentially exterior to the crocheted strap.

9. A crocheted anti-static wristband having an upper surface, a lower surface, opposing longitudinal ends and opposing transverse edges, said wristband comprising:
   upper and lower weft yarns traversing between said opposing transverse edges of the wristband and generally respectively forming said upper and lower surfaces thereof;
   a plurality of longitudinally extending elastic threads positioned between said upper and lower weft yarns;
   a plurality of electrically conductive yarns positioned beneath said lower weft yarn; and
   a plurality of warp yarns forming an interlocking series of loop stitches which serve to bind said upper and lower weft yarns with said plurality of elastic threads therebetween and said plurality of electrically conductive yarns thereunder.

10. The crocheted anti-static wristband of claim 9 wherein said plurality of electrically conductive yarns further comprises:
    a plurality of parallel yarn lengths connected to and running substantially along the longitudinal direction of the wristband.

11. The crocheted anti-static wristband of claim 9 wherein said plurality of electrically conductive yarns are arranged in generally serpentine paths so as to permit longitudinal expansion and control of said electrically conductive yarns in accordance with said wristband.

12. The crocheted anti-static wristband of claim 9 wherein said electrically conductive yarns are adequately visible upon the wristband as to permit visual determination of the physical and electrical continuity of said electrically conductive yarns.

13. The crocheted anti-static wristband of claim 12 wherein at least some of the electrically conductive yarns are of a contrasting color to the underlying wristband, thereby facilitating visual determination thereof.

* * * * *